US006258263B1

(12) United States Patent
Henderson et al.

(10) Patent No.: US 6,258,263 B1
(45) Date of Patent: Jul. 10, 2001

(54) LIQUID CHROMATOGRAPH ON A CHIP

(75) Inventors: H. Thurman Henderson, Cincinnati; Neville R. deGouvea-Pinto, Loveland, both of OH (US)

(73) Assignee: The University of Cincinnati, Cincinnati, OH (US)

( * ) Notice: Subject to any disclaimer, the term of this patent is extended or adjusted under 35 U.S.C. 154(b) by 0 days.

(21) Appl. No.: 09/398,847

(22) Filed: Sep. 17, 1999

(51) Int. Cl.[7] .................................................. B01D 15/08
(52) U.S. Cl. ........................ 210/198.2; 210/656; 204/451; 204/601; 422/70
(58) Field of Search ........................................ 204/600, 601, 204/602, 603, 604, 605, 451, 452, 453, 454, 455, 456, 450; 210/635, 656, 659, 198.2; 422/68.1, 69, 70

(56) References Cited

U.S. PATENT DOCUMENTS

| 5,116,495 | * | 5/1992 | Prohaska | 210/198.2 |
|---|---|---|---|---|
| 5,165,292 | * | 11/1992 | Prohaska | 210/198.2 |
| 5,376,252 | * | 12/1994 | Ekstrom | 210/198.2 |
| 5,500,071 | * | 3/1996 | Kaltenbach | 210/198.2 |
| 5,571,410 | * | 11/1996 | Swedbeeg | 210/198.2 |
| 5,641,400 | * | 6/1997 | Kaltenbach | 210/198.2 |
| 5,658,413 | * | 8/1997 | Kaltenbach | 210/198.2 |
| 5,792,943 | * | 8/1998 | Craig | 210/198.2 |
| 5,888,390 | * | 3/1999 | Craig | 210/198.2 |
| 5,935,430 | * | 8/1999 | Craig | 210/198.2 |
| 6,136,187 | * | 10/2000 | Zare | 210/198.2 |

* cited by examiner

Primary Examiner—Ernest G. Therkorn
(74) Attorney, Agent, or Firm—Wood, Herron & Evans, LLP

(57) ABSTRACT

A chromatograph fabricated using microelectromechanical techniques. The chromatograph includes a first layer superimposed over a second layer. At least one micro-channel is etched into the second layer to provide the separation column of the chromatograph. The surfaces of the micro-channel are chemically activated in order to separate the components of a sample flowing through the micro-channel by bonded phase chemistry. A third layer is placed in superimposed relationship with the second layer. At least one pair of electrodes is formed to the third layer with at least a portion of the electrodes internal to the micro-channel of the second layer. The electrodes detect separated components flowing through the micro-channel and identify them by their electrical conductivity. The depth of the micro-channel is greater than the width, thereby minimizing pressure drop across the device and allowing the chromatograph to operate with a high degree of speed, sensitivity and accuracy. Good resolution is obtained with narrow integrated electrodes for sensing the separated components of the sample.

32 Claims, 4 Drawing Sheets

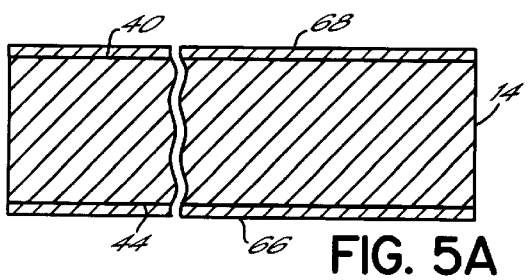
FIG. 5A
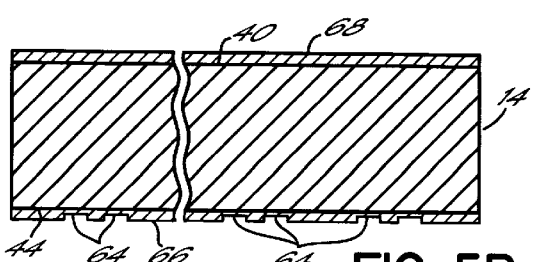
FIG. 5B
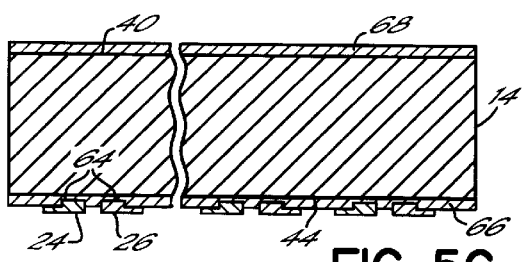
FIG. 5C
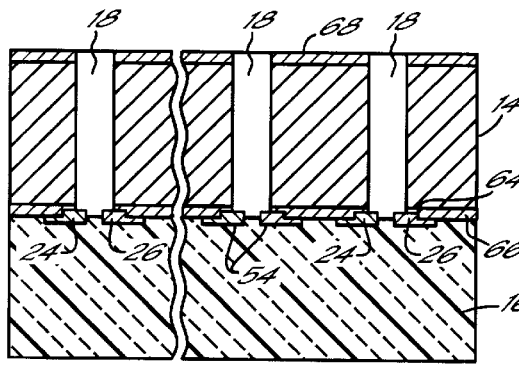
FIG. 5D
FIG. 5E
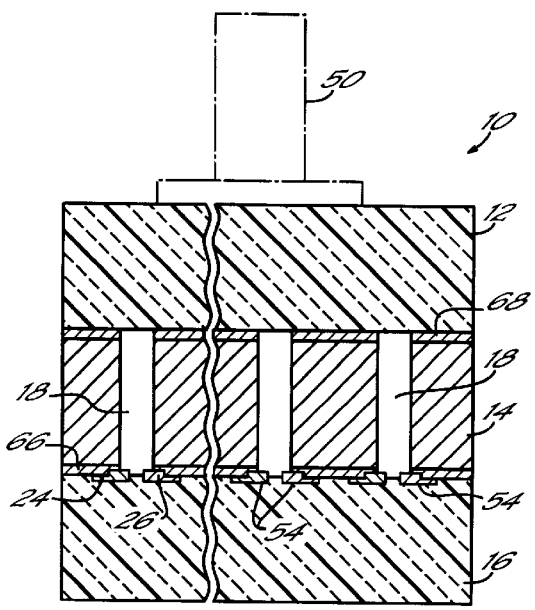
FIG. 5F
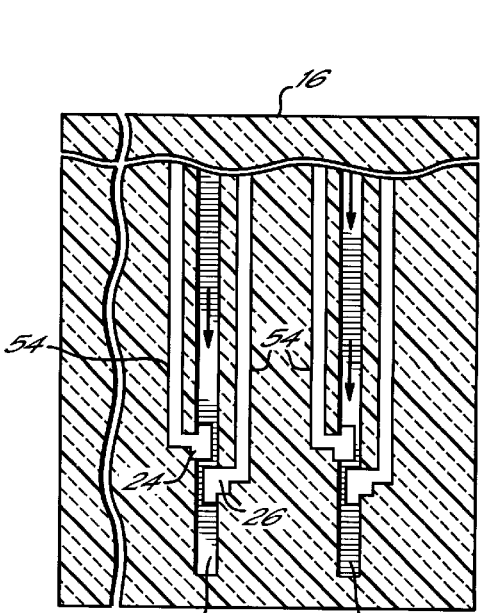
FIG. 6

LIQUID CHROMATOGRAPH ON A CHIP

FIELD OF THE INVENTION

The invention generally relates to microelectromechanical system (MEMS) devices and methods of making the same, and more particularly, to a chromatograph micromachined using MEMS technology.

BACKGROUND OF THE INVENTION

Liquid chromatography is one of the most widely used techniques for separation and analysis of liquid samples. Liquid chromatographs are used as the apparatus for analyzing samples. Liquid chromatography is a method of chemical separation that involves passage of a liquid phase through a solid phase and relies on subtle chemical interactions to resolve complex mixtures into pure compounds. In a liquid chromatograph, a sample is mixed with a carrier. The components of the sample are separated while flowing through a separation column, and sample components are fixed and identified by referring to a resulting chromatogram. A liquid chromatograph employs a material that is located in a separation column and selected depending on a sample to be analyzed. This material comprises the stationary phase of the liquid chromatograph. The liquid phase carrier transports the sample through the stationary phase. Thermodynamic differences in the interaction of components of the sample with the mobile (liquid) and stationary (usually a solid) phases causes the components to separate. This phenomenon produces a chromatogram which can subsequently be used to identify the components of the sample.

Certain stationary phases utilize relative ionic bond strength to cause the components of a sample to separate. Ion exchange is typically used for separation and determination of organic and inorganic ions in complex mixtures. In ion exchange separation, the stationary phase has charge-bearing functional groups. The sample components then compete with the mobile phase ion for ionic sites on the stationary phase. This bonding allows one to tailor the surface chemistry of this phase to give virtually any desired interaction.

Conventional chromatographs are bulky pieces of lab equipment. Such cumbersome pieces of equipment are also not amenable to transport and/or use at remote locations. Other important practical problems associated with conventional chromatographs include high-solvent consumption and long analysis time. As such, they cannot be used for on-line process control and real time data monitoring on a continual basis. Typically, an assay run through these liquid chromatographic systems can require from at least thirty minutes to over sixty minutes to complete a sample analysis. For example, analysis of amino acids is an arduous and lengthy process because of the many components to be analyzed. The standard assay of amino acids can take up to thirty minutes and the physiological fluid assay may require as much as 110 to 140 minutes to complete.

The time required for processing creates additional problems. Chemical sensor technology for on-line sensing is currently lagging behind needs, particulary in the chemical and pharmaceutical industries, in environmental monitoring, and for a wide range of medical applications. Due to the length of time on-line or real time detection is not an option for most applications. This limitation can have profound consequences. For example, in the chemical process industry, product quality and process safety are often directly influenced by the speed with which accurate and reliable chemical composition data can be obtained. The traditional approach to on-line chemical detection has been to develop highly selective sensors. While this approach has had some noticeable successes, it has also been plagued with a variety of difficulties, primarily in developing suitable selective sensors for the enormous variety of problems faced. Thus, it would be advantageous to shorten the time required to analyze a sample.

One method by which the analyzing time of a conventional liquid chromatograph can be shortened is by reducing the size of resin particles filled in the separation column. However, one problem with this size reduction of the resin particles is that they have a tendency to pack together. Once this compaction occurs, gravity is unable to singularly urge the liquid or mobile phase of the chromatograph through the separation column. This problem has been overcome through the use of a highly pressurized system to force the liquid phase to pass through the solid phase in the chromatographic column. This sort of chromatography is referred to as "high pressure" or "high performance" liquid chromatography (HPLC). However, the reductions in size of resin particles does not involve a corresponding reduction in the size of the chromatographic equipment to a degree that would facilitate use of the chromatograph for remote sensing.

One method of reducing the size of the chromatograph and other such devices is through the application of microelectromechanical systems (MEMS) technology. New applications and uses for microelectromechanical systems are continuously being developed. Many of these systems typically include one or more microactuated devices that are batch micromachined into silicon wafers or other substrates in part using many of the photolithographic batch fabrication techniques developed for fabricating electronic devices, except that the etching is expanded into the third dimension. Microactuated devices typically include movable members or components that are either driven by an electrical stimulus to perform mechanical tasks or are sensory elements that generate an input into an electronic system in response to a physical stimulus or condition. In addition, by virtue of the commonality of many manufacturing processes, control and other support electronics may also be fabricated onto the same substrates as the microactuated devices, thereby providing single chip solutions for many microelectroinechanical applications.

The general approach in trying to miniaturize a chromatograph, or any other device, involves copying the function of the device as it exists on a macro-scale. On a macro-scale, efficiency in a chromatograph is enhanced by minimizing the distance that molecules of sample have to travel prior to being adsorbed onto the surfaces of the solid particles that are normally present in chromatographic systems. The primary way to achieve this minimization is to reduce the diameter of the separation column.

However, reducing the size of a chromatograph by using microelectromechanical system technology can result in additional drawbacks. Such a miniaturized chromatograph will be unable to utilize the filled column solid phase which is found in high performance liquid chromatography (HPLC), any filler particles being simply too large for the separation component of the chromatograph. As a result, open tubular liquid chromatography (OTLC) is often used as an alternative approach to the conventional filled column of HPLC. Studies have demonstrated that OTLC can provide results in some aspects comparable, and in some aspects greatly superior, to those typically attained using the conventional HPLC apparatus. For a good performance, an OTLC column must be made very narrow (less than 10 micrometers in diameter) which at the same time requires an adequate sample injection system and detector cell of comparably small volumes. This small size of the separation column makes OTLC amenable for use in a chromatograph fabricated using MEMS technology.

Another problem that immediately presents itself upon such a severe reduction in size of the separation column, is the increased pressures that occur across the device. Most of the problems and limitations in the development of OTLC micro-channels are related to the high pressure involved in pumping liquids through the miniature structures, which are typically formed as shallow cavities isotropically or anisotropically etched in silicon. In a macro-system chromatograph, there is essentially no limitation on the pressure drop because a pump can be built to a size sufficient to pump the carrier through the separation column in a very uniform velocity profile. In reducing a chromatograph to the microlevel, one is unable to utilize conventional pumping technology to maintain such a uniform velocity profile. Yet, these pressures must be kept low in order for the chromatograph to function properly. Often, prior separating devices would use a "V"-shaped groove. However, these structures do not address the pressure drop issue nor the desirability of a maximum active surface area in the channel with small diffusion lengths and minimal consumption of lateral surface "real estate". Thus it would therefore be advantageous to develop alternative geometries.

Currently, due to numerous specific applications, there is a great need for the realization of such a miniature chromatographic system. Whereas V-grooves can be realized by micromachining crystalline wafers around in the (100) orientation, all of the above requirements can be uniquely realized by fabrication of a chromatograph by MEMS technology utilizing (110) silicon process technology, which would result in atomically smooth, narrow, vertical channels, the ultimate in stacking efficiency (minimum chip "real estate") and advantages such as small size, light weight, low cost, high resolution and high throughput. Furthermore, fast analysis and possible on-chip integration of supporting electronic circuitry for signal analysis and remote control would enable sensing on a remote location.

A chromatograph that meets the above criteria and is developed with (110) silicon microelectromechanical systems batch processing technology will need to be fabricated with at least three essential components: (1) a pump, (2) a separating device, and (3) a detector. Microelectromechanical systems technology has been recently used to develop micropumps and microsensory devices. However, to date there has been virtually no development of a separating device in microscale that can achieve the necessary reductions in pressure and no previous efforts have been reported in (110) silicon. Development of such a separating device is necessary to the development of a chromatograph built with microelectromechanical systems technology.

Thus, it would be desirable to develop a chromatograph which does not exist as a bulky piece of lab equipment involving long assay times and high solvent consumption. Additionally, it would be desirable to develop a chromatograph wherein a sample is completely separated prior to detection. Moreover it is desirable to minimize the diffusion distance from the channel center to the active surface in order to achieve fast time response and high sensitivity, which uniquely requires deep narrow slots with vertical walls of the type achievable in (110) silicon. Finally, it would be desirable to develop a chromatograph on a microscale without the problems of experiencing a high degree of pressure across the device.

SUMMARY OF THE INVENTION

The chromatograph of the present invention typically utilizes non-conventional (110) silicon microelectromechanical systems technology to fabricate a liquid chromatograph having micro-channels that are less susceptible to pressure drop than OTLC configurations of the prior art while allowing maximum stacking efficiency for minimal volume concentration due to the vertical defining channel walls possible in (110) silicon anisotropic etching. As a result, the present invention provides a chromatograph which allows for on-line or real time chemical detection without a high degree of pressure drop across the device.

In general, the chromatograph of the present invention includes at least a first layer operatively connected to a second layer. The second layer includes the separating device of the chromatograph. This separating device is in the form of at least one micro-channel anisotropically etched deeply into the surface of the second layer. This micro-channel is deeper along the longitudinal axis of the channel than it is wide, thereby minimizing the pressure drop across the device while achieving other advantages. At least one detector is formed on, and as an integral part of, at least one of the layers, with a portion of the detector being exposed to an internal portion of the micro-channel, so as to detect the separated sample components. Detection devices such as electrodes, ultra-violet light, visible light, lasers, infra-red light, and refractive index may be employed as well, and may be so interacted monolithically on chip. Fluid inlet and outlet ports are disposed in the first layer. The fluid inlet port is operatively connected to the micro-channels by a series of fingers, which are microfluidic conduits extending between the two components. A feed reservoir is located adjacent the proximal end of each micro-channel and a waste reservoir is located adjacent to the distal ends of the micro-channels to a waste reservoir. As the sample passes through the micro-channel, it is separated into its constituent components by bonded-phase chemistry as a result of chemically activated sites on the surfaces of the micro-channels. As the separated components pass over at least one pair of electrodes and out of the micro-channels, the electrodes detect the components of the now-completely separated sample.

The novel structure of the micro-channels whereby the depth is much greater than the width is referred to as deep channel geometry. Such channels may be anisotropically etched in (110) single crystalline silicon by surface alignment of optical lithographic patterning so as to expose slow etching (111) vertical planes using KOH or other well-known chemical anisotropic etchants in the MEMS community. With deep channel geometry the mobile or liquid phase of the chromatographic system will be exposed to a very large active surface area as it moves through the micro-channels. In the chromatograph of the present invention, the width of each micro-channel is kept to the small clearances required for the rapid transfer of molecules to its chemically activated surface to enhance sensitivity and time response. By increasing the depth of each micro-channel, the liquid phase carrier experiences very little resistance in the direction of flow. As such, the pressure drop across the device is effectively minimized. Pressure drop may be further reduced using "stacked" parallel channels.

More particularly, in the chromatograph of the present invention an ion-exchange separator comprising a plurality of micro-channels, including an integrated electrical conductivity detector for micro-liquid chromatography, is disclosed. The separator has been fabricated on a silicon chip, and has a novel open slit configuration of micro-channels, whereby the depth of each micro-channel is much greater than the width, in order to enhance separation efficiency without an excessive pressure drop. The surfaces of the micro-channels have been chemically activated for anion exchange.

Specifically, the micro-channels are etched on a (110) crystalline silicon wafer. These micro-channels are linear and exhibit no discontinuity in cross-section along the longitudinal axis of the micro-channel. The channels may be linear or folded in a serpentine configuration following available (111) type crystallographic planes for further dimensional reduction. The micro-channels are enclosed on the top side by an electrostatically bonded compatible glass wafer, typically of a borosilicate type. The micro-channels may also be enclosed on the bottom with an electrostatically bonded glass wafer. "Fingers" extending from the inlet port disposed in the glass wafer bounding the top side of the micro-channels transport the liquid carrier material through the glass wafer and to the micro-channels. These fingers align directly with the micro-channels. The ends of each finger include reservoirs adjacent the micro-channels: a feed reservoir at the proximal end and a waste reservoir at the distal end. The reservoirs and fingers are designed to ensure that each flow path experiences the same pressure drop. Specially fabricated (or plastic or metallic) glass nipples are bonded to the top glass wafer to enable a connection to an external pumping system and to collect liquid carrier. As the liquid phase proceeds along the flow path for the device, mixing in the liquid is minimized, particularly in a simple linear configuration.

Electrodes are lithographically deposited at the bottom of the silicon micro-channels in pairs to detect the analytes as they elute from the separation column. The electrodes are placed using conventional silicon dioxide microprocessing, common to microelectronic planar processing. These electrodes are fabricated from gold, or other conductive material, and are formed on one of the layers of the chromatograph with at least a portion of the electrode exposed to and integral with the interior of the micro-channels. The electrodes, which may be configured to measure along or across the micro-channel, are connected by metal lines to bonding pads, which are in turn connected by standard wire bonding techniques to external bonding pads for electrical connections.

Thus, the present invention provides a chromatograph with on-line impedance detectors for ion detection, based on open tubular liquid chromatography (OTLC) principles. In addition to narrow micro-channels to serve as separation columns, reservoirs for liquid inlet and outlet are present. The connections from the micro-channels to an external pumping system are realized typically using custom made glass nipples in zero dead volume fittings. The objects and advantages of the present invention are further appreciated in light of the following detailed description and drawings in which:

BRIEF DESCRIPTION OF THE DRAWINGS

FIGS. 5A–5F are schematics demonstrating the method of fabrication of a chromatograph in accordance with the principles of the present invention.

FIG. 6 is a cross-sectional view of the fabrication of the chromatograph of the present invention taken along lines 6—6 of FIG. 4A.

DETAILED DESCRIPTION

Figure 1A:
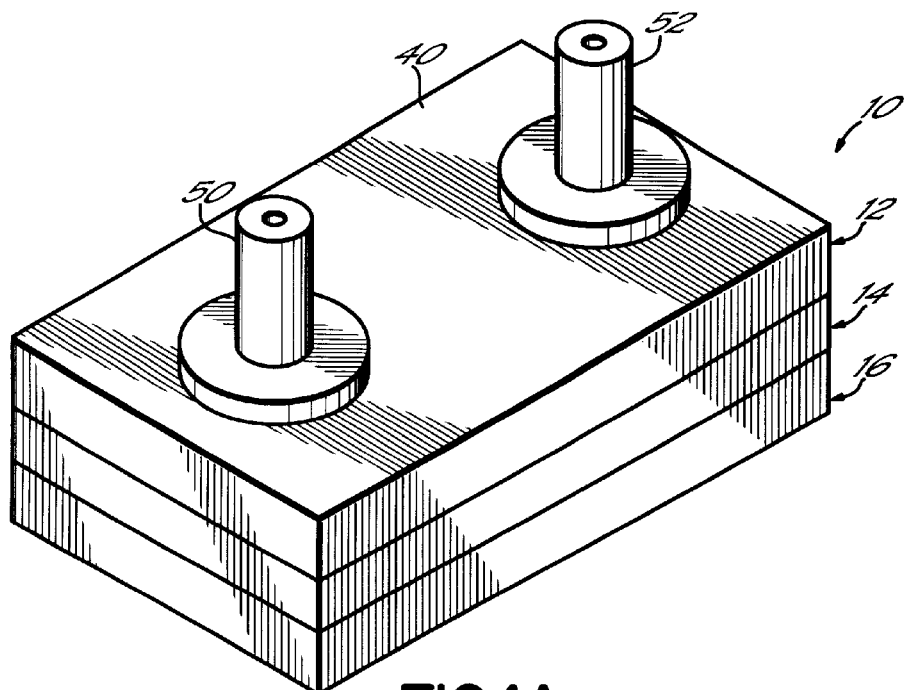
FIG. 1A is a perspective view of a chromatograph fabricated with microelectromechanical techniques in accordance with the principles of the present invention.
Figure 1B:
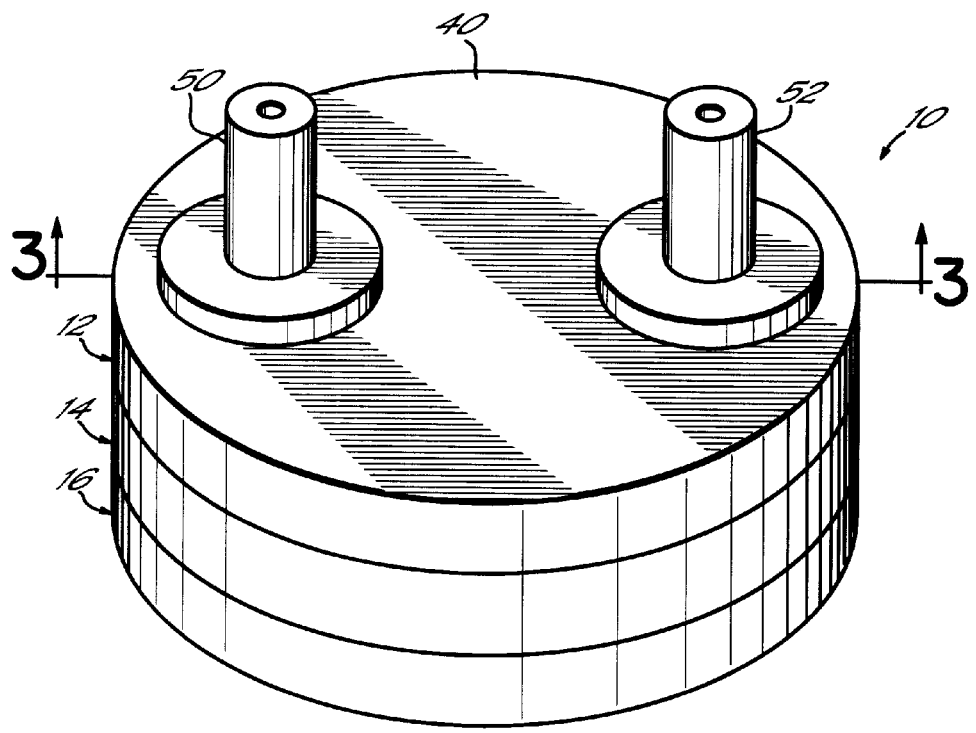
FIG. 1B is a perspective view of a chromatograph including annular wafers fabricated with microelectromechanical techniques in accordance with the principles of the present invention.
Figure 2:
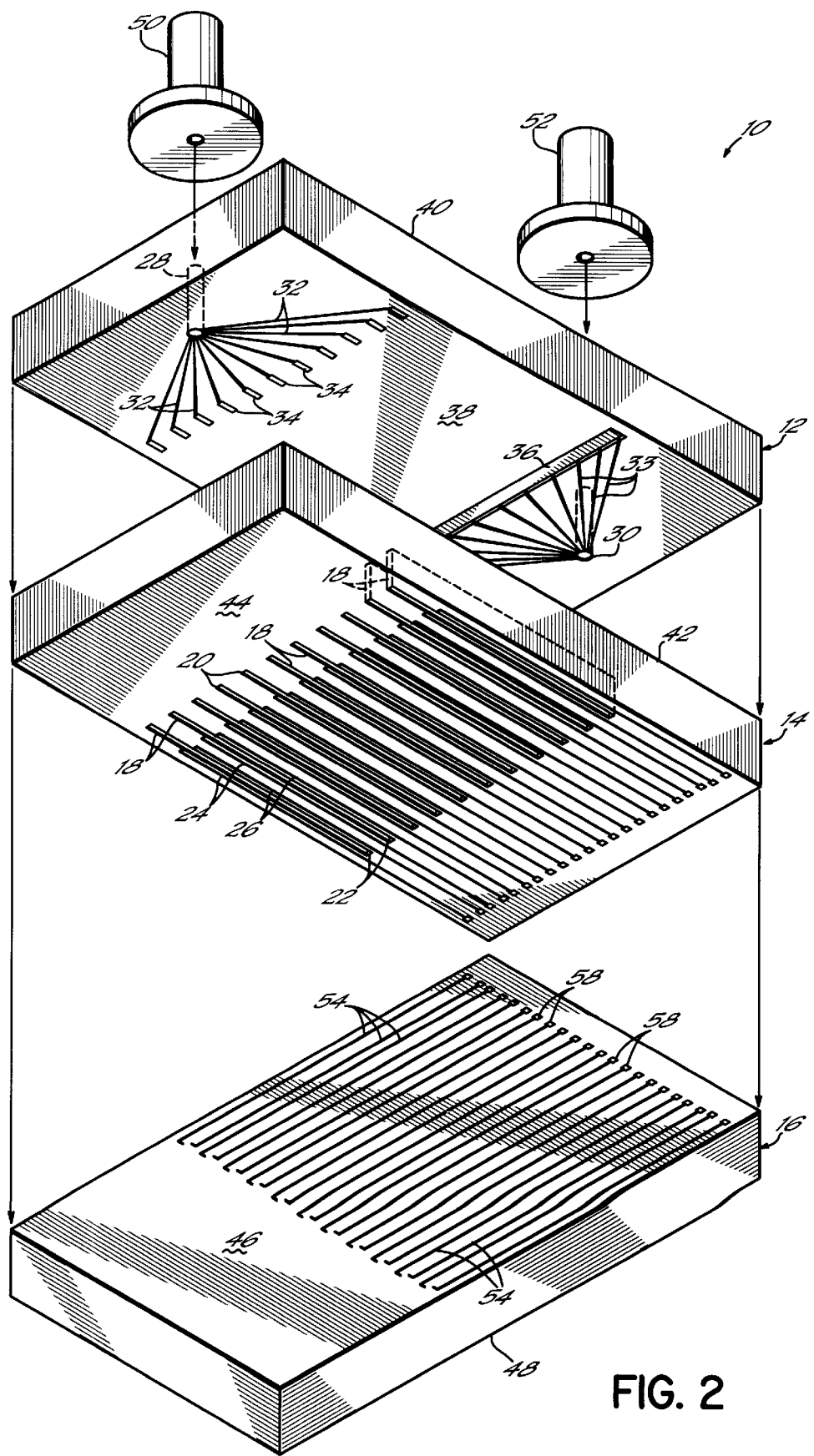
FIG. 2 is an exploded view of the chromatograph fabricated with microelectromechanical techniques showing etchings disposed in each layer.

As shown in FIGS. 1 and 2, a MEMS technology fabricated liquid chromatograph 10 consistent with the principles of the present invention includes a first layer 12 overlying a second layer 14. At least one micro-channel 18 is etched into the second layer 14 to act as a separator for the chromatograph 10, analogous to the separating device of open tubular liquid chromatography and the filled column in high performance liquid chromatography as described in the background of the invention. Each micro-channel 18 has a proximal end 20 and a distal end 22 and the surfaces of these micro-channels 18 are chemically activated with functionally charged groups. In the illustrated embodiment, a third layer 16 is associated with the second layer 14 on a side opposite that of the first layer 12. The third layer 16 creates a bottom surface boundary for the micro-channels 18 in the illustrated embodiment wherein the micro-channels 18 are etched completely through the silicon of the second layer 14.

Figure 4:
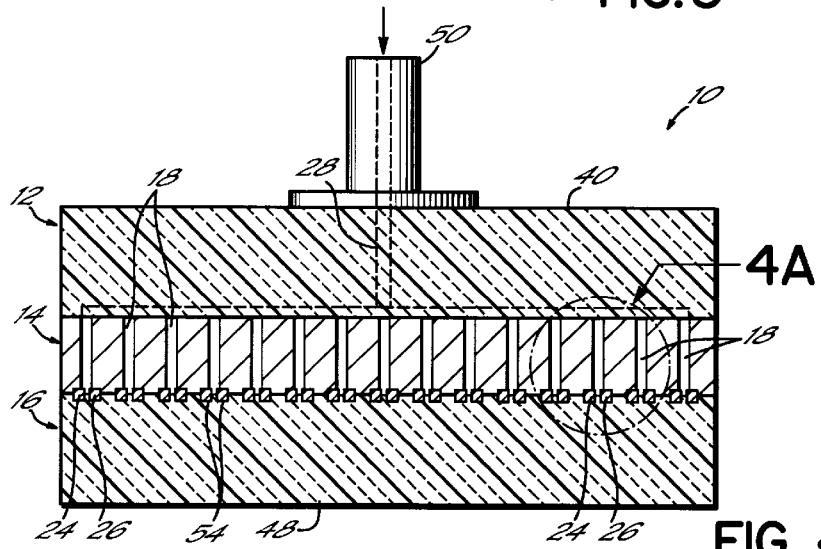
FIG. 4 is a schematic of the chromatograph of the present invention taken in cross-section along lines 4—4 of FIG. 3 demonstrating the placement of electrodes within a plurality of micro-channels.
Figure 4A:
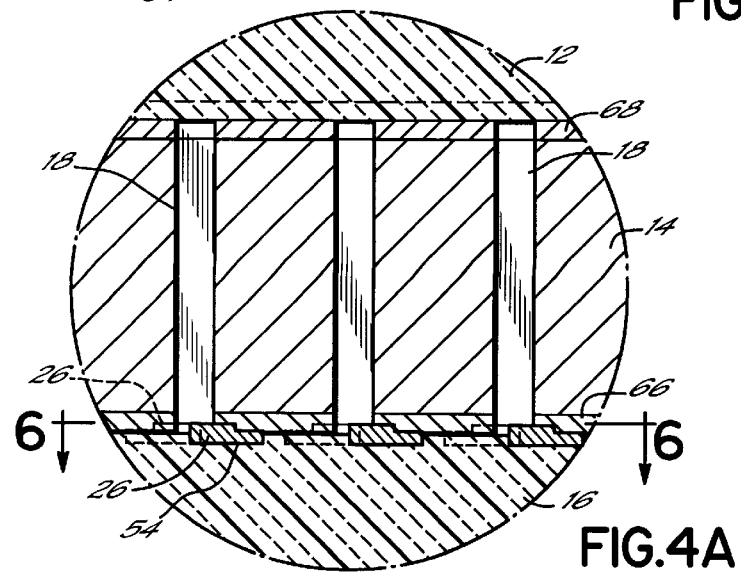
FIG. 4A is an enlarged view of the chromatograph of the present invention taken from the encircled portion 4A of FIG. 4.

One pair of electrodes 24, 26 is formed onto layer 16 of the chromatograph 10 with at least a portion of the electrodes 24, 26 exposed to and integral with an internal portion of a micro-channel 18 (FIG. 4A). The electrodes can be formed on layer 12 or 14 if desired and anywhere along the length or depth of the micro-channel 18 and anywhere along the length or depth of the micro-channel 18 and more than one pair can be employed if desired. These electrodes 24, 26 operate as detectors for the chromatograph 10. As the components of a sample proceed through the micro-channel 18, they are separated by the chemically activated surfaces of the micro-channels 18. The electrodes 24, 26 then measure the conductivity of each component as the carrier passes over the electrodes 24, 26 in order to identify the components.

The first layer 12 overlying the second layer 14 of the chromatograph 10 includes a fluid inlet port 28 and a fluid outlet port 30. The inlet and outlet ports 28, 30 are orifices disposed through the first layer 12 from the exposed side 40 to the opposite or bonding side 38. A series of "fingers" 32, which are non-circular tubular conduits for the liquid carrier phase, radiate from each fluid inlet port 28 and are operatively connected to a corresponding micro-channel 18. These fingers 32 are etched into the bonding side 38 of the first layer 12 of the chromatograph 10 and transport liquid carrier containing sample to be analyzed from the inlet port 28 to the proximal ends 20 of the micro-channels 18. Once the sample has been analyzed, additional fingers 33 transport waste carrier to the outlet port 30 of the chromatograph 10. A feed reservoir 34 is integral with the fingers 32 etched into a surface of the first layer 12. This feed reservoir 34 includes a portion of the fingers 32 adjacent to the proximal end 20 of the micro-channels 18 and serves to buffer the flow of the liquid carrier through the micro-channels 18. A waste reservoir 36 is integral with the fingers 33 etched into the surface of the first layer 12. Glass nipples 50, 52 are fabricated onto the exposed side 40 of the first layer 12, and are associated with and circumferential about the inlet and outlet ports 28, 30 of the chromatograph 10 of the present invention. The waste reservoir 36 includes a portion of the fingers 32 adjacent to the micro-channels 18 at their distal ends 22.

If the chromatograph 10 included only first and second layers 12, 14, the second layer 14 would include a bonding side 42, associated with the first layer 12, and side 44 would be exposed. In the illustrated embodiment of the present invention, a second bonding side 44 of the second layer 14 is associated with the third layer 16 of the chromatograph 10. In the illustrated embodiment, wherein the chromatograph 10 includes a third layer 16, the third layer 16 includes a bonding side 46, which is associated with the second bonding side 44 of the second layer 14, and an exposed side 48, which is not associated with any layer. In the illustrated embodiment of the chromatograph 10, the first layer 12 is positioned to overlie the second layer 14 and the second layer 14 is positioned to overlie the third layer 16, as shown in FIG. 1.

Although the illustrated embodiment of the invention discloses a single silicon wafer as the second layer 14 of the chromatograph 10, in alternate embodiments of the chromatograph 10, the second layer 14 may include multiple (110) silicon wafers in a vertically stacked configuration. In stacking multiple wafers and aligning the micro-channels 18 of each wafer with each adjacent wafer, it is possible to create a second layer 14 including micro-channels 18 with a depth much greater than that which could be achieved with a single silicon wafer. By this method, the depth of the micro-channels 18 of the chromatograph 10 of the present invention is not limited by the thickness of commercially available wafers.

In the illustrated embodiment shown in FIG. 2, the first layer 12 is in the shape of an annular wafer having a diameter and a thickness. However the upper surface profile may be rectangular or of an arbitrary shape. The diameter of the first layer 12 is in the range of about 20 to 150 millimeters. The thickness of the first layer 12 is in the range of about 0.05 to 0.75 millimeters. This first layer 12 may be comprised of any nonconductive material amenable to etching techniques, including glass or silicon. In the illustrated embodiment of the present invention, the first layer 12 is comprised of glass.

Figure 3:
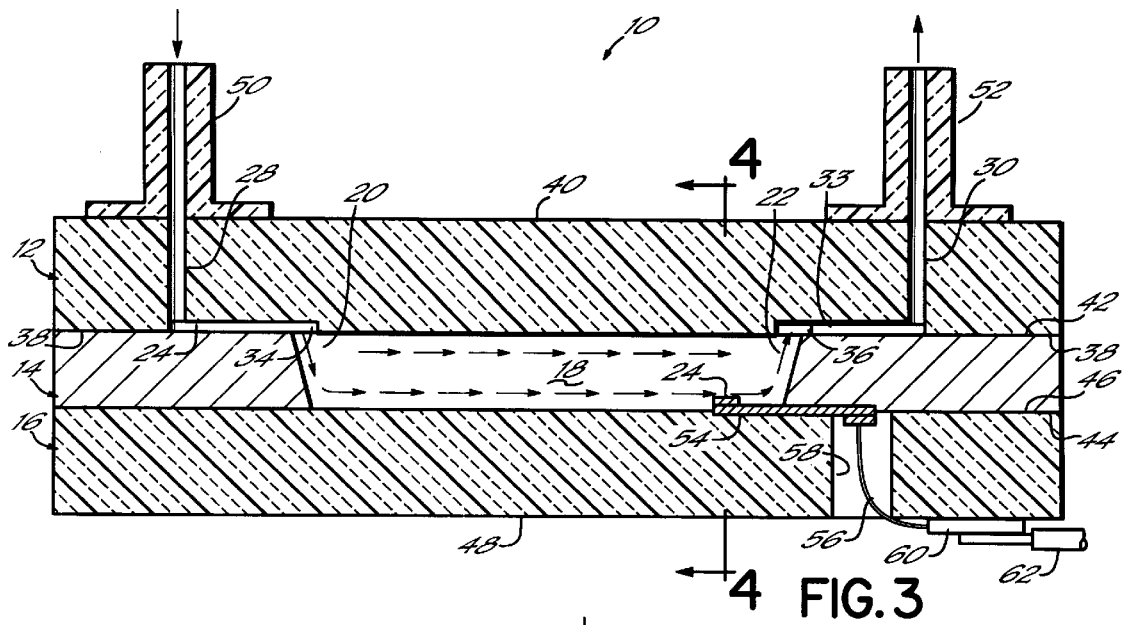
FIG. 3 is a cross-sectional view of the chromatograph of the present invention taken along lines 3—3 of FIG. 1B showing the flow path of the liquid phase in the chromatograph.

Orifices of both the inlet and the outlet ports 28, 30 have a diameter in the range of about 0.01 to 0.8 millimeters. A nipple 50 is located about the fluid inlet port 28 adjacent to and circumferential about the orifice of the inlet port 28, as shown in FIGS. 2 and 3. In the illustrated embodiment, the nipple 50 is fabricated from glass. The glass nipple 50 has an inner diameter of 0.01 to 0.8 millimeters and is associated with and integral about the circumference of the fluid inlet port 28. The glass nipple 50 has an outer diameter of 6.25 millimeters and a height of 25.4 millimeters. The glass nipple 50 is bonded to the exposed side 40 of the first layer 12 by various bonding techniques including electrostatic bonding, adhesives, etc. In the illustrated embodiment of the chromatograph 10 of the present invention, the glass nipple 50 associated with the fluid inlet port 28 of the first layer 12 is bonded to the first layer 12 with adhesive. Associated with the fluid outlet port 30 is a similar outlet glass nipple 52 having an inner diameter of 0.01 to 0.8 millimeters associated with and integral with the diameter of the fluid outlet port 30 of the first layer 12. This outlet glass nipple 52 has an outer diameter of 6.25 millimeters and a height of 25.4 millimeters. This glass nipple 52 is bonded about the fluid outlet port 30 of the first layer 12 with adhesive. These lead to fingers 32 and 33.

Fingers 32 are etched into the bonding side 38 of the first layer 12 and radiate from the inlet port 28 to the proximal ends 20 of each of the micro-channels 18 of the second layer 14, with each finger 32 being associated with a particular micro-channel 18. These fingers 32 are etched into the first layer 12 in a manner orthogonal to the inlet port 28. The fingers 33 provide a direct passage for liquid phase carrier from the inlet port 28 to the micro-channels 18. The area of each finger 33 disposed immediately adjacent the proximal end 20 of the micro-channel 18 comprises the feed reservoir 34. The feed reservoir 34 serves to buffer the flow of the liquid carrier through the micro-channels 18. Alternatively, each finger 32 may proceed from a separate inlet port to a particular micro-channel 18.

Additional fingers 33 are etched into the bonding side 38 of the first layer 12 and radiate from the outlet port 30 to a waste trough 36 adjacent the distal end 22 of the micro-channels 18. These fingers 33 are etched into the first layer 12 in a manner orthogonal to the outlet port 30. The fingers 33 provide a direct passage for liquid phase carrier from the waste trough 36 to the outlet port 30. Alternatively, the fingers 33 may radiate from the outlet port 30 directly to the distal ends 22 of the micro-channels 18 of the second layer 14, with each finger 33 being associated with a particular micro-channel 18. In another alternative embodiment, each finger 33 may proceed from a particular micro-channel 18 to separate outlet ports.

The inlet port 28 of the chromatograph 10 is operatively connected to a stock (not shown) containing liquid phase carrier and sample to be analyzed. The glass nipple 50 surrounding said inlet port 28 is operatively connected to an external pumping system (not shown) used for transporting carrier and sample into the inlet port 28 and subsequently through the fingers 32 and micro-channels 18 of the chromatograph 10. The outlet port 30 and outlet glass nipple 52 are operatively connected to a waste storage area (not shown) for depositing separated sample following analysis in the chromatograph 10.

In the illustrated embodiment depicted in FIGS. 2 and 3, the second layer 14 is in the shape of an annular wafer having a diameter and a thickness. The diameter of the second layer 14 is in the range of about 20 to 150 millimeters. The thickness of the second layer 14 is in the range of about 0.005 to 100 millimeters. This second layer 14 typically is comprised of (110) silicon which has a degree of electrically insulating silicon dioxide surface within the channels but may be any nonconductive substance amenable to appropriate photolithographic etching, plasma etching or MEMS micro-forming techniques. Such materials include silicon, quartz, germanium and various polymeric materials, although (110) silicon has relevant and appropriate characteristics. In the illustrated embodiment of the present invention, the second layer 14 is comprised of silicon. It should be noted that the second layer 14 of the chromatograph 10 need not be in wafer form, but may be of any shape to facilitate etching of micro-channels 18 for separation of sample components in a chromatograph 10. In the illustrated embodiment, the second layer 14 is utilized in wafer form so that conventional planar photo litographic wafer processing may be performed.

In the illustrated embodiment shown in FIGS. 2 and 3, the third layer 16 of the chromatograph 10 is in the shape of an annular wafer having a diameter and a thickness. The diameter of the third layer 16 is in the range of about 20 to 150 millimeters. The thickness of the third layer 16 is in the range of about 0.05 to 0.75 millimeters. The third layer 16 may be comprised of any nonconductive material amenable to photolithographic etching techniques. Such materials include glass or silicon. In the illustrated embodiment of the present invention, the third layer 16 includes glass. The third layer 16 also includes etchings 54 for use in seating electrodes 24, 26 into the third layer 16, with the electrodes 24, 26 at least partially extending into the micro-channels 18 of the second layer 14. These etchings 54 also seat metal lines 56 for connecting the electrodes 24, 26 to bonding pads 60. An orifice 58 disposed through the third layer 16 provides an opening for metal lines 56 extending from electrodes 24, 26 to external bonding pads 60 for connection of those components during analysis and detection of separated samples. The structure and function of electrodes 24, 26, metal lines 56, and bonding pads 60 will be discussed below.

As shown in FIGS. 2, 3, 4 and 4A, at least one micro-channel 18 having proximal and distal ends 20, 22 is etched into the second layer 14 of the chromatograph 10 of the present invention by photolithographic etching techniques. In the illustrated embodiment, a plurality of micro-channels 18 are etched into the second layer 14. Simultaneous multiple analysis in chromatography is an attractive capability, so far not available in conventional chromatographic systems. In the micro-chromatograph 10 however, it may be realized by batch fabricating several parallel micro-channels 18 on a single silicon wafer. The same analysis can be carried out in numerous parallel channels, in which case if for any reason one analysis fails, the result can be read from another micro-channel 18. Alternatively, if each micro-channel 18 is chemically activated for different species identification, a single device might be used for a different analysis instead of replacing a separation column prior to each analysis. Although the second layer 14 may contain several such micro-channels 18, the illustrated embodiment of the chromatograph 10 exhibits a representative number of micro-channels 18 etched into the second layer 14 silicon wafer. Those skilled in the art will appreciate the increased number of laterally "stacked" integrated micro-channels 18 that may be etched into the second layer 14 of the chromatograph 10 using standard photolithographic etching techniques. In the illustrated embodiment, each micro-channel 18 is linear and has a length, a width, and an aspect ratio. The aspect ratio is determined by obtaining the quotient of the depth of the micro-channel 18 divided by the width of the micro-channel 18 (depth/width). In the illustrated embodiment of the chromatograph 10, the micro-channels 18 have a length in the range of about 0.4–150 millimeters, a width in the range of about 0.001–0.250 millimeters, and an aspect ratio in the range of about 5–400 with a preferred value of about 100 within a preferred range of 5–150.

As can be determined by the non-fractional value of the aspect ratio, the depth of the micro-channels 18 of the illustrated embodiment of the present invention is greater than the width of the micro-channels 18. This configuration of the micro-channels 18 is referred to as "deep channel geometry" and reduces and minimizes pressure drop across the device to a degree not found in micro-devices of the prior art. Reduction in size of the chromatograph 10 to that of a MEMS technology device would typically increase in pressure across the device which prevents the proper functioning of the chromatograph 10. The width of the micro-channel 18 must be kept small to keep the ions of the sample confined close to the chemically activated surface of the micro-channels 18 to thereby enhance separation. By extending the depth of the micro-channels 18 to achieve the aspect ratios of the present invention, increased pressure is dissipated across the device, resulting in more accurate operation of the chromatograph 10. Additionally, due to the increased depth of the micro-channels 18, the carrier of the liquid phase moving through the cross-sectional area of the chromatograph 10 will be exposed to a very large active surface area of the micro-channel 18. Thus, the deep channel geometry results in the fabrication of a chromatograph that is not only highly successful in minimizing pressure drop across the device, but maximizes the surface area of the micro-channels to which sample is exposed, which is where chromatographic activity occurs.

One parameter that has been used in measuring the efficiency of bench scale chromatographic systems is referred to as the "number of theoretical plates". This parameter is calculated from the resulting peaks in a chromatogram. The width of a peak at a particular location on its height axis is compared with the width of peaks produced by different chromatographs having tested the same material and normalized for retention time. A wider peak on the resulting chromatogram corresponds to a lower number of separation plates. The larger the number of theoretical plates, the better the efficiency of the chromatograph 10. The number of theoretical plates is a good parameter for measuring the efficiency of bench scale systems because it merely calculates the separation efficiency of the system and does not consider the cost by which that separation efficiency is achieved. The cost of separation efficiency in a chromatograph 10 results from the pressure drop across the device, which is equivalent to the energy that you are putting into the system. Thus, a parameter is used to calculate the efficiency of the system along with the cost-effectiveness of the system. This parameter is often used with microdevices and is known as the "separation impedance". The separation impedance takes into account the number of theoretical plates combined with the pressure drop realized in a micro-chromatograph 10. The smaller this number, the more efficient the process in the chromatograph 10. With deep channel geometry as developed in the present invention, the microchromatographs 10 of the present invention exhibit separation impedances which are incredibly small. Separation impedances of the low value exhibited by the present chromatograph 10 have not yet been achieved by competing devices. Thus, deep channel geometry of the chromatographs 10 of the present invention have a tremendous advantage in minimizing pressure drop over chromatographs of the prior art.

Although the micro-channels 18 of the illustrated embodiment are linear, in alternate embodiments the micro-channels 18 may have a serpentine shape (not shown). In this alternate embodiment, the micro-channel 18 is "folded" to give a serpentine configuration with an effective length of the order of 10,000 millimeters. The folds in this serpentine configuration create sections of the micro-channel 18 that are parallel with the longitudinal axis proceeding from the inlet port 28 to the outlet port 30 and sections which are perpendicular to the longitudinal axis of the micro-channel 18, or in the case of (110) silicon follow the appropriate {111} vertical planes in the folded bends.

During passage through the micro-channels 18 of the second layer 14 of the chromatograph 10 of the present invention, the liquid carrier passes over the detector, which analyzes each separated component in order to identify the components of the sample. In the illustrated embodiment, this detector comprises at least one pair of electrodes 24, 26 formed on one of the layers 12, 14, 16 of the chromatograph 10. These electrodes 24, 26 preferably include conductive materials (i.e., gold, copper, aluminum, etc.)

Referring to FIGS. 3, 4 and 4A, in the illustrated embodiment of the present invention, gold electrodes 24, 26 are deposited at the bottom of the silicon micro-channels 18 to detect the separated analytes of the sample as they proceed through the micro-channels 18. The electrodes 24, 26 may be located anywhere along the length and depth of the micro-channel 18. There may be single or multiple electrode pairs in a single micro-channel 18. In the illustrated embodiment, the electrodes 24, 26 are fabricated on the second layer 14 of the chromatograph 10 with at least a portion of the pair of electrodes 24, 26 extending into the micro-channels 18 of the second layer 14. Thus, the detector of the chromatograph 10 of the present invention is integral with the separator. The electrodes 24, 26 are of a rectangular shape, approximately 10 $\mu$m×100 $\mu$m. The electrodes 24, 26 are not limited to this rectangular shape and have an area in the range of about 0.000025 millimeters$^2$ to 0.01 millimeters$^2$.

The electrodes 24, 26 are connected by metal lines 56 to bonding pads 60, which are in turn connected by standard wire bonding techniques to external bonding pads 62 for electrical connections. The metal lines 56 interconnecting the electrodes 24, 26 one to another and to the bonding pads 60 of the chromatograph 10 have a width in the range of 0.005 millimeters to 1 millimeters. Like the electrodes 24, 26, the lithographically formed thin film metal lines 56 of the chromatograph 10 may include any appropriate conductive metal. The bonding pads 60 have an area in the range of 0.0001 millimeters$^2$ to 1 millimeters$^2$. The forming of these components to the chromatograph 10 will be discussed with the fabrication of the chromatograph 10 below.

In general, the fabrication process of the chromatograph 10 of the present invention begins with the thermal oxidation of the silicon wafer of the second layer 14 of the chromatograph 10, as best shown in FIGS. 5A–5E. Thermally grown oxide serves two purposes: it acts as an insulating layer between the silicon and metal patterns, and it protects the silicon during wet etching, typically in potassium hydroxide (KOH). Moreover an ultra thin oxide layer spontaneously forms on the surface walls of the micro-channels during processing which is instrumental to the ultimate device operation. In the illustrated embodiment, the oxidation of the second layer 14 was performed in three steps: dry oxidation for 30 minutes followed by the wet oxidation for 7 hours and dry oxidation for an additional 30 minutes. In the illustrated embodiment, the thickness of the thermally grown oxide layer is about 1.2 $\mu$m for KOH etching. Contact windows 64 are then opened on the oxide layer 66 on the bottom side 44 of the second layer 14, followed by photolithography, chromium/gold evaporation and lift-off (FIGS. 5A and 5B). After the metal pattern is defined on the bottom side 44 of the second layer 14, the micro-channels 18 are aligned to this pattern and exposed from the top side 42 of the second layer 14. Isotropically etched channels, however, do not result in high aspect ratios. Intermediate results may be obtained with reactive ion etching and deep reactive ion etching (DRIE). After opening windows in the top side oxide 68 for micro-channels 18 to be etched, the wafer of the second layer 14 is immersed into an aqueous KOH solution. Micro-channels 18 are then etched through the silicon wafer second layer 14 by standard photolithographic etching techniques that will be appreciated by those skilled in the art, after which electrodes 24, 26 are exposed from the bottom side of the second layer 14 (FIG. 5D). These micro-channels 18 can be isotropically etched into the second layer 14 or, alternatively, can be anisotropically etched into the second layer 14. Isotropically etched channels, however, do not result in high aspect ratios. Intermediate results may be obtained with reactive ion etching (RIE) and deep reactive ion etching (DRIE). These fabrication steps are based on standard silicon and MEMS fabrication techniques. The forming of electrodes 24, 26 in the chromatograph 10 of the present invention will be described in detail later.

Following oxidation, a standard lithography process for the positive resist is used to transfer the desired features to the silicon surface of the second layer 14 using high resolution photographic masks. During this process, an adhesion promoter coating (HMDS) is applied to the second layer 14, by spin coating equipment, to help in adhering the photoresist to the silicon oxide surface, thereby reducing the degree underetching during the oxide etching process. After the HMDS and photoresist is spun on the bottom side of the second layer 14, the silicon wafer is soft baked. Following baking, resist is exposed through the first mask, developed in positive resist developer, mixed with deionized (DI) water, and hard baked. The oxide on the side of the second layer 14 to be associated with the first layer 12 of the chromatograph 10 is protected by spinning on the adhesion promoter and resist, using the same procedure as described above. Openings in the photoresist are etched in buffered hydrofluoric acid (BHF) for a period of time sufficient to remove the necessary amount of oxide. In the illustrated embodiment, these openings are etched for approximately five minutes in order to remove 0.5 $\mu$m oxide, as the determined etching rate of oxide in BHF is 0.1 $\mu$m/minute. After etching, and after the resist is removed by soaking the second layer 14 in acetone and methanol, the wafer is base cleaned and dried prior to the second lithography step.

The second lithography is also performed using the same mask. The photoresist needs to be lifted-off, thereby removing the unnecessary metal from the surface of the second layer 14. The purpose of this step is to fill up the windows in the oxide with metal. After HMDS and resist are spun onto the second layer 14, the soft bake is performed followed by an exposure period, as described above. The second layer 14 is then soaked in chlorobenzene, dried with nitrogen and developed. After developing, the second layer 14 is dried with nitrogen and hard baked. No DI water is used in this lithography procedure.

Following the above two lithography steps, a metalization process is performed. This metalization allows for the formation of metal contacts with liquids. In the illustrated embodiment, chromium/gold layers are used. The initial chromium layer is used to promote surface adhesion. Chromium/gold layers are used in metalization due to their resistance to KOH during silicon etching, as well as their low reactivity with chemicals during the surface activation of the micro-channels 18. However, one problem associated with the use of gold on silicon is related to its low eutectic temperature, which is usually exceeded during electrostatic bonding. Notwithstanding an insulating layer of oxide between gold and silicon, the gold may diffuse into the silicon through small pin-holes in the oxide layer when the temperature is higher than that of the eutectic temperature of gold. As a result, the standard electrostatic bonding procedure has been modified in this work, in order to perform the bonding at lower temperatures, and will be described in detail below.

Following the metalization process, a lift-off procedure is performed. During this procedure, a positive resist stripper (such as Baker 3000 in the illustrated embodiment) is heated. The second layer 14 is then dipped in the solution, and typically after about 5–10 minutes the resist is removed from the silicon surface of the second layer 14, together with any unnecessary metal. A second lithography for lift-off was performed on the side of the second layer 14 associated with the third layer 16 of the chromatograph 10 in the illustrated embodiment. This lithography lift-off utilizes a mask and is followed by a second metalization procedure identical to that described above. Chromium/gold is evaporated to form the electrodes 24, 26, bonding pads 60 and interconnecting metal lines 56 to the chromatograph 10. The same lift-off procedure as described above was repeated. The second layer 14 at this state of fabrication is depicted in FIG. 5C.

Following the above procedures, the second layer 14 silicon wafer is rinsed in DI water, soaked in acetone and methanol and rinsed in DI water. After drying in an oven overnight, the micro-channels 18 are etched by the following technique. An infrared device (not shown) is first used to align a third mask to the metal pattern on the bottom side 44 of the second layer 14 and to open cavities in the oxide 68 for the etching of micro-channels 18. This alignment procedure is important in order to ensure that the electrodes 24, 26 formed to the chromatograph 10 will be exposed to the interior of the micro-channels 18, once they are etched into the second layer 14 The bottom side 44 of the second layer 14 which includes the metal patterns for electrodes 24, 26 was protected with resist so that the oxide 66 could not be removed from that side. BHF is then used to etch micro-channels 18 in the oxide on the top side of the second layer 14. Following etching, the resist is removed by soaking the second layer 14 in acetone and methanol, and rinsing in DI water.

The rate and quality of anisotropic silicon etching, using potassium hydroxide (KOH), depends largely on the temperature and concentration of the etching solution. In the illustrated embodiment, the best results are obtained with an aqueous 45% KOH solution heated to 40° C., which results in smooth micro-channel 18 side walls, and an insignificant degree of underetch. Beneficially, the gold electrodes 24, 26 are not damaged by etching at 40° C., as is the case at higher temperatures. Following etching, the bottom side oxide 66 was exposed as a "bridge" over the micro-channels 18. These oxide bridges were usually broken, due to the stress in oxide thermally grown on the silicon of the second layer 14.

Following the above-described etching process, the second layer 14 is electrostatically bonded to the first and third layers 12, 16. By bonding to the second layer 14, the glass wafer of the third layer 16 seals the micro-channel 18 etch through the second layer 14 from its second bonding side 44. However, the thickness of the metal and oxide 66 of the second layer 14 prevent any association between the second and third layers 14, 16 intimate enough to allow for electrostatic bonding between the two layers. To eliminate this problem, shallow cavities 54 are etched into the bonding side 46 of the glass wafer of the third layer 16 in which to seat the electrodes 24, 26, bonding pads 60, and metal lines 56 of the chromatograph 10, thereby bringing the surfaces of the second and third layers 14, 16 into intimate association with one another to permit electrostatic bonding. In the illustrated embodiment, hydrofluoric acid (HF) is used to etch glass. The HF etching rates, are largely dependent on the size of the window to be etched. Therefore, chromium/copper is evaporated to protect the areas not to be etched, followed by the lithographic procedure described above to open windows in the metal. The fifth mask is used to open these windows. Copper was then electroplated using a DC current to achieve a more reliable protective layer and to fill the pin holes inherent in the evaporated layer. By this method, HF only attacks the glass exposed in the openings in the metal defined by the lithography. During this electroplating, the third layer 16 is rotated in order to achieve uniform copper thickness.

Since the etching depth in the glass trench 54 in the third layer 16 needs to match the height of the metal pattern on the silicon surface of the second layer 14, the etching time is kept short, generally only about 13.5 seconds in the illustrated embodiment of the invention. After etching, copper and chromium are removed. The glass wafer of the third layer 16 is then metalized again on the opposite side 48. The same procedure described above is repeated using another mask to create through-holes 58 in the bottom 48 of the third layer 16 in order to open windows for accessing the bonding pads 60, 62 after the completed device is sealed. After the through holes 58 are etched, the copper is removed and the glass wafer third layer 16 is base cleaned for electrostatic bonding to the silicon wafer of the second layer 14.

The same lithography, backside protection and glass etching procedures described above for the third layer 16 glass wafer are followed to create fingers 32 in the glass wafer of the first layer 12 to operatively connect the micro-channels 18 of the second layer 14 with the liquid inlet and outlet ports 28, 30 of the first layer 12. The fourth mask is used to transfer the pattern of fingers 32, 33 including reservoirs 34, 36 to the first layer 12.

After etching is complete, the three layers 12, 14, 16 are bonded one to another by electrostatic bonding. Electrostatic bonding is a well known technique commonly used for hermetically sealing silicon to glass, at temperatures below the softening point of the glass. There are several requirements necessary for electrostatic bonding to take place. These include the need for the glass to be slightly conductive at the bonding temperature, the silicon and glass surfaces roughness to be less than 1 micron, and the thermal coefficient of expansion of the silicon and glass to be closely matched to avoid cracking upon cooling. Mirror polished silicon wafers as well as borosilicate glass used in this process, will meet these requirements. The electrostatic bonding is usually performed at an elevated temperature in the range of about 420° C. and a 1000V to 1500V potential. A thin intermediate silicon dioxide layer can be tolerated in this bonding method.

In the chromatograph 10 of the present invention, the electrostatic bonding needs to be achieved at a lower temperature due to the presence of gold electrodes 24, 26 on the silicon surface, although the underlying chromium layer prevents the eutectic from forming. If a lower temperature is not used, the eutectic temperature may be reached at about 370° at pin holes. For the silicon to glass bonding in the chromatograph 10 of the present invention, a temperature of about 350° C. and a potential of about 800V are applied in a vacuum environment. Following heating with pressure the wafers of the first, second and third layers 12, 14, 16 are allowed to cool down for about 2 hours.

Following electrostatic bonding of the layers, the glass nipples 50, 52 are associated with the fluid inlet and outlet ports 28, 30 of the first layer 12 of the chromatograph 10. After the first layer 12 is patterned from one side for fingers 32, the inlet and outlet ports 28, 30 are drilled through the first layer 12 to connect the fingers 32, 33 with the exposed side of the first layer 12. This is done by using a glass blower and commercially available drill bits. In the illustrated embodiment, the glass nipples 50, 52 are bonded to the glass wafer of the first layer 12 using G-10117 Glass Transfer Tape, which is specifically designed for sealing and joining PYREX® parts. The material is designed to be applied in a thin layer and consequently, PYREX® parts can be fused without cracks or stress due to thermal expansion mismatch. This process was successfully used instead of direct fusing of PYREX® parts. The bonding process in the illustrated embodiment is as follows: parts to be bonded were placed on the adhesive layer of the glass tape. Subsequently, they were pressed using a pressure in the range of about 1–20 psi for a period of approximately 1 minute. The sealing procedure started at room temperature with a pressure in the range of about 5–20 psi on the parts to be sealed to insure proper flow of the molten glass. The temperature was then raised to about 490–540° C. in 30–40 minutes, using an inert gas atmosphere and held for about 15–25 minutes. The minimum cooling time was about 30–40 minutes.

Following the bonding process, the surfaces of the micro-channels 18 are chemically activated. The micro-channels 18 etched in the second layer 14 operate as a separator for the chromatograph 10 of the present invention. The micro-channels 18 of the chromatograph 10 of the present invention operate in a manner analogous to the separation column in a conventional chromatograph. However, the present invention uses the principles of ion exchange through bonded-phase selectivity in the micro-channel walls to separate the components of the sample. Ion exchange with bonded-phases is often used as a separation method in open-tubular liquid chromatography (OTLC). These bonded phases provide efficient, highly reproducible stationary phases in the chromatograph 10. This bonding also allows one to tailor the surface chemistry of solid phase particles to give virtually any desired interaction. In OTLC, the side walls of the separation column are chemically activated to separate sample components in a carrier. The small size of the micro-channels 18 in the chromatograph 10 of the present invention does not allow for any solid particles bearing functional groups to be present within the channel. Thus the surface walls of the micro-channels 18 are chemically activated as in OTLC.

Different separation mechanisms in liquid chromatography can be realized by bonding different chemical groups to the surface of silica to produce bonded phases. In the chromatograph 10 of the present invention, a thin silica layer is formed on the silicon micro-channels 18 of 10 to 20 Å or more when exposed to an aqueous solution. There are numerous chemical methods which can be used to produce a variety of bonded phase structures on the surface. For an OTLC column, the ideal choice is a bonded phase produced by using monofunctional silanes, as they provide a stationary phase on the order of 25 to 100 Å, are reproducible, exhibit excellent mass transfer properties (which result in high column separation efficiency) and possess known surface morphology.

In the chromatograph 10 of the present invention, techniques have been developed for immobilizing ion exchange groups on the oxidized silicon wafers of the second layer 14 to facilitate chemical separations. A two step synthesis has been adopted to modify the oxidized silicon surface for an amine functionality.

In the illustrated embodiment of the present invention, surface activation is performed in a flow process consisting of a reservoir connected to a conventional HPLC pump (such as a Spectra-Physics, Model 8800). The fluid is pumped past a pre-column, used to protect downstream elements from contamination, into a pre-heater, which is connected by an appropriate Swagelock or similar fitting to the inlet glass nipple of the first layer 12 of the chromatograph 10. The surface activation process involves two major steps: surface modification and immobilization of charged sites on the modified surface. The chemistry of these steps is as follows.

For the silicon/silicon dioxide surface modification, in the illustrated embodiment of the invention, a 10% (v/v) 3-glycidoxypropyltrimethoxysilane in toluene solution, pre-heated to 120° C. in the pre-heater, is pumped through the micro-channels 18 for 16 hours using an HPLC pump at a flow rate of 0.1 ml/min. The second layer 14 is then dried in a vacuum oven at 15–20 inch Hg and 50° C. to remove any unreacted silane in the micro-channels 18. The micro-channels 18 are then cleaned by pumping acetone through them at a flow rate of 0.1 m./mn for 1.5 hours, and then drying in a vacuum oven at 15–20 inch Hg at room temperature for 16 hours.

The surface charge of the illustrated embodiment of the present invention was introduced with polyethyleneimine. Immobilization of this compound is achieved by pumping 20% (w/v) polyethyleneimine (MW=600) in methanol solution through the micro-channels 18 at a flow rate of 0.1 ml/min at room temperature for 16 hours. The second layer 14 is then heated in a vacuum oven at 50° C. for 12 hours to accelerate the immobilization reaction. After heat treatment, the second layer 14 is washed with methanol and acetone for half an hour each at 0.1 ml/min, and then dried in a vacuum oven at room temperature for 12 hours.

In use, a sample to be analyzed is mixed with a liquid phase carrier and deposited through the fluid inlet port 28 of the first layer 12, where it proceeds through the fingers 32 including feed reservoirs 34 in the first layer 12 to the proximal end 20 of the micro-channels 18 of the second layer 14. As the carrier flows through the micro-channels 18, the charged surfaces of the micro-channels 18 separate the sample into its constituent components, which then pass over and are identified by the electrodes 24, 26 partially exposed to the micro-channels 18. The separated sample then flows out of the distal end 22 of the micro-channels 18 back through fingers 33 and out through the fluid outlet port 30 in the first layer 12. By fabricating with microelectromechanical systems (MEMS) technology, the chromatograph 10 of the present invention may be used at remote locations and offer analysis data on-line or in real time for many applications.

There is therefore provided a miniaturized chromatographic system fabricated using MEMS technology utilizing silicon process technology. This chromatograph exhibits the advantages of small size, light weight, low cost, high resolution and throughput. Additionally, fast analysis and possible on-chip integration of supporting electronic circuitry for signal analysis and remote control would enable sensing on a remote location. Finally, the deep channel geometry of the micro-channels 18 of the present invention minimize the pressure drop across the device.

While the present invention has been illustrated by the description of various embodiments thereof, and while these embodiments have been described in considerable detail, it is not the intention of the Applicant to restrict or in any way limit the scope of the appended claims to such detail. Additional advantages and modifications will readily appear to those skilled in the art. The invention in its broader aspects is therefore not limited to the specific details, representative system and method, and illustrative example shown and described. Accordingly, departures may be made from such details without departing from the spirit or scope of Applicant's general inventive concept.

What is claimed is:

1. A chromatograph comprising:
a first layer, having a thickness and a second layer having a thickness, said second layer having a top side and a bottom side, said first layer in a superimposed relationship with said top side of said second layer;
at least one micro-channel etched into said second layer having a depth into said second layer and a width, wherein the depth of said micro-channel is greater than the width of said micro-channel;
at least one pair of electrodes formed on the chromatograph, at least a portion of said pair of electrodes being exposed to an internal portion of said micro-channel;
a fluid inlet port disposed in said first layer and operatively connected to said micro-channel; and
a fluid outlet port disposed in said first layer and operatively connected to said micro-channel;
whereby fluid passing through said inlet port and into and through said micro-channel will be chromatographically separated into components and pass over said pair of electrodes and out of said micro-channel and to said outlet port.

2. The chromatograph of claim 1 further comprising a third layer having a thickness, said third layer in a superimposed relationship with said bottom side of said second layer.

3. The chromatograph of claim 2 wherein said at least one pair of electrodes is formed on said third layer.

4. The chromatograph of claim 2 wherein said third layer is annular.

5. The chromatograph of claim 4 wherein the diameter of said third layer is in the range of about 20 millimeters to about 150 millimeters.

6. The chromatograph of claim 5 wherein the thickness of said third layer is in the range of about 0.5 millimeters to about 0.75 millimeters.

7. The chromatograph of claim 6 wherein said third layer includes glass.

8. The chromatograph of claim 7 wherein said third layer is electrostatically bonded to said bottom side of said second layer.

9. The chromatograph of claim 1 includes wherein said second layer includes silicon.

10. The chromatograph of claim 9 wherein said second layer is annular.

11. The chromatograph of claim 10 wherein the diameter of said second layer is in the range of about 20 millimeters to about 150 millimeters.

12. The chromatograph of claim 11 wherein the thickness of said second layer is in the range of about 0.005 millimeters to about 100 millimeters.

13. The chromatograph of claim 1 wherein the width of said micro-channel is in the range of about 0.001 millimeters to about 0.250 millimeters.

14. The chromatograph of claim 13 wherein said micro-channel has an aspect ratio of about 5 to about 400.

15. The chromatograph of claim 1 wherein the surfaces of said micro-channel are chemically activated.

16. The chromatograph of claim 15 wherein said surfaces are chemically activated by 10-glycidoxypropyltrimethoxysilane.

17. The chromatograph of claim 15 wherein said surfaces are chemically activated by polyethyleneimine.

18. The chromatograph of claim 15 wherein said surfaces are chemically activated by polyethyleneimine in methanol.

19. The chromatograph of claim 1 wherein said at least one pair of electrodes includes gold.

20. The chromatograph of claim 19 wherein each electrode of said at least one pair of electrodes has an area in the range of about 0.000025 millimeters$^2$ to about 0.01 millimeters$^2$.

21. The chromatograph of claim 1 wherein said at least one pair of electrodes is operatively connected to a first bonding pad having an area in the range of about 0.001 millimeters$^2$ to about 1 millimeter$^2$.

22. The chromatograph of claim 21 wherein said at least one pair of electrodes is operatively connected to said first bonding pad by metal lines, said metal lines having a width in the range of about 0.005 millimeters to about 1 millimeter.

23. The chromatograph of claim 22 wherein said first bonding pad is operatively connected to an external second bonding pad having an area in the range of about 0.0001 millimeters$^2$ to about 1 millimeter$^2$.

24. The chromatograph of claim 1 wherein said first layer includes glass.

25. The chromatograph of claim 24 wherein said first layer is annular.

26. The chromatograph of claim 25 wherein the diameter of said first layer is in the range of about 22 millimeters to about 153 millimeters.

27. The chromatograph of claim 26 wherein the thickness of said first layer is about 0.6 millimeters to about 0.78 millimeters.

28. The chromatograph of claim 27 wherein said first layer is electrostatically bonded to said top side of said second layer.

29. The chromatograph of claim 1 further comprising a plurality of micro-channels and said inlet port is operatively connected to said micro-channels by fingers radiating from said inlet port through said first layer and to said micro-channels for transporting carrier from said inlet port to said channels.

30. The chromatograph of claim 29 further comprising a first nipple associated with said first layer and circumferential about said fluid inlet port, whereby said first nipple is operatively connected to an external pumping system for introducing a carrier through said first nipple and into said fluid inlet port.

31. The chromatograph of claim 30 wherein said outlet port is operatively connected to said micro-channels by fingers radiating from said outlet port through said first layer and to said micro-channels for transporting carrier from said micro-channels to said outlet port.

32. The chromatograph of claim 31 further comprising a second nipple associated with said first layer and circumferential about said fluid outlet port, whereby said second nipple is operatively connected to an external pumping system for depositing a carrier through said second nipple and out through said fluid outlet port.

* * * * *